US00PP09237P

United States Patent [19]

Klemm

[11] Patent Number: Plant 9,237

[45] Date of Patent: Aug. 8, 1995

[54] GERANIUM PLANT 'KLEHISP'

[76] Inventor: Siegfried Klemm, Hanfäcker 8, D 70378 Stuttgart, Germany

[21] Appl. No.: 286,013

[22] Filed: Aug. 4, 1994

[51] Int. Cl.[6] ..... A01H 5/00
[52] U.S. Cl. ..... Plt./87.12
[58] Field of Search ..... Plt. 87.12

[56] References Cited

U.S. PATENT DOCUMENTS

P.P. 6,716 4/1989 Duemmen ..... Plt./87.12

*Primary Examiner*—James R. Feyrer
*Attorney, Agent, or Firm*—Arnold, White & Durkee

[57] ABSTRACT

Geranium Klehisp is a new and distinct cultivar of geranium, botanically known as *Pelargonium*×*zonale* Hybriden. It is distinguished from other geranium plants by its dark red color and unusually dark green foliage combined with a regular compact appearance.

1 Drawing Sheet

BACKGROUND OF THE NEW PLANT

Klehisp is a product of a controlled breeding program that has the objective of developing new geranium plants with an elegant, warm red flower on self-branching dark leafed plants with a further objective of improving both Klesec and Kleflam, which are two varieties with dark leaves and red flowers.

Klehisp originated from the seed parent Klesec, (U.S. Plant Pat. No. 7,873) and pollen parent Kleflam (U.S. Plant Pat. No. 8,551). Klesec has been commercially available since 1990. Kleflam is also the result of a controlled breeding program and was commerically available from 1991 until 1993. Klehisp was substituted for Kleflam in the commercial market in 1993. Klesac is marketed under the tradename Ecco. Kleflam is marketed under the tradename Flamenco. Both plants are protected in BSA Hannover/Germany under Plant Breeders Protection Rights.

The new cultivar was discovered in 1990 and selected by the inventor as one flowering plant from among the progeny of the seed parent Klesac and the pollen parent Kleflam grown in a controlled environment in Stuttgart, Germany. The seed from Klesac was obtained after pollination of Klesac with the pollen parent Kleflam. Klehisp differs from its seed parents. Klehisp has large dark red single flowers. There are 6–7 long, wide petals and only a few petaloids. Klehisp grows compactly, giving an overall different appearance from either parent, in part because of the more regular compact growth habit. By comparison, seed parent Klesec has orange-red double flowers and 7–8 petals with 1–3 petaloids. The petals are short and wide, giving a somewhat disordered and fluffy appearance. The pollen parent Kleflam has dark red flowers with a bluish tone and a flower shape similiar to Klesec.

Compared with its seed parent Klesec, Klehisp has a shorter, more compact and regular habit than Klesec which is a medium high, medium self-branching bushy plant, but not very compact. Klehisp differs from its pollen parent Kleflam, in showing a more uniform appearance, but is otherwise similiar in its deep red or dark red color.

The first act of asexual reproduction of Klehisp was accomplished when vegitative cuttings were taken from the initial selection in a controlled environment in Stuttgart, Germany, by the inventor or technicians working under the supervision of the inventor. Horticultural examination of the selected plants demonstrated that the combination of characteristics herein disclosed for Klehisp are firmly fixed and are retained through successive generations of asexual reproduction.

Klehisp has not been observed under all possible environmental conditions. The phenotype may vary significantly with variations in environment such as temperature, light intensity, and day length. The following observations, measurements, and comparisons describe plants grown in Stuttgart, Germany, under conditions that approximate those used in commercial practice. Similar characteristics are found when the plant is grown under controlled environmental conditions in Germany, Italy, Teneriffe, and The Netherlands.

Of the many varieties of the same species of geranium plant, the new cultivar Klehisp is judged to most closely resemble the Goldsmith varieties known as Americana Cherry Red, as well as Tango. Pelfi Tango is similar in having dark red flowers with dark green foliage, but has a different flower shape. Klehisp is earlier producing than Tango, and has a much more regular growth, grows more compactly and the plant is shorter. Klehisp is earlier, more floriferous and appears to be somewhat less weather resistant. To the inventor's knowledge, both Tango and Klehisp are suitable for all climates. Klehisp propagates very well, as does Tango, based on inventor's information concerning Tango. Flower color of Klehisp is a little different from Tango, but beacuse of its broad petals and cupped-shaped semi-double flowers, Klehisp has a more elegant and orderly appearance than Tango which has more "fluffy" flowers.

The overall appearance of Klehisp is attractive due to the flowers that are borne on vertical stems over the very regular and compact, round plants. The universal acceptance and use of the Klehisp variety of geranium gives it a high market value.

DESCRIPTION OF THE PHOTOGRAPH

The accompanying color photograph of Klehisp illustrates typical inflorescence and leaf characteristics of the new plant. The plant was photographed using professional photographic techniques. The view is taken against a blue background that illustrates flower color closest to the color values in accordance with the Royal Horticultural Society Colour Chart. The blue background highlights the deep, rich velvety red color of the flowers.

DESCRIPTION OF THE PLANT

The following description uses color references from the Royal Horticultural Society Colour Chart. The color values were determined under prevailing conditions of natural daylight in a greenhouse environment during the month of March in Stuttgart, Germany.

The following traits have been repeatedly observed and are determined to be basic characteristics of Klehisp that in combination distinguish this geranium as a new and distinct cultivar. These characteristics include the deep red flower color that contrasts with the dark green foliage and compact growth habit.

Classification:

*Botanical.*—*Pelargonium*×*zonale* Hybriden.

*Commercial.*—Klehisp, Zonale Geranium.

The plant:

*Form.*—Bush.

*Shape.*—Round, symmetrical.

*Height.*—April-May, when marketable.—200 mm. End of season.—270 to 300 mm.

*Time from rooted cutting to flowering.*—93 days (under commerical greenhouse conditions).

*Growth rate.*—Medium.

*Pinching to induce branching.*—Not required, the plant is highly self-branching from basal nodes.

*Stem length.*—110–120 mm (less if outdoors in heat).

*Leaf stem length.*—40–60 mm (depends on temperature and light).

*Branching character.*—Good.

*Number of stems per stalk.*—5.

*Number of stalks per plant.*—2 to 3.

*Height.*—Compact.

*Internode length.*—11–12 mm.

*Foliage:* Quantity.—Mediumn to moderately dense, leaves are less dense than on plants of similar varieties and are smaller. Shape.—Reniform, basal lobes overlap close to the sinus. Margin type.—Bicrenated. Size.—4.5–5 cm in length and 7–8 cm in width. Texture: Old leaves.—Leathery. Young leaves.—Smooth. Color: Upper side.—147A. Underside.—147B. Zonation.—Discernable, usually inconspicuous, except for weak zonation if the nights are cold, lacking red or brown coloration.

Inflorescence:

*Blooming habit.*—Continuous (no pinching necessary). While this plant continues to bloom, remontance can be enhanced by removing spent blossoms. Blossoms will appear continuously without picking old flowers.

*Blooms.*—Profuse.

*Blooming period.*—Early blooming from April and continuously until frost.

*Size of cluster.*—Measured when more than 20 florets are open.

*Diameter.*—100–110 mm.

*Depth.*—95 mm.

*Size.*—4.8–5.2 cm diameter.

*Petalage.*—68.

*Florets.*—Number of florets per cluster.—35. Size.—60 mm diameter. Fullness.—Semi-double. Shape.—Cup-shaped when florets first open becoming more flat with maturity. Perfect.—Yes, contains both pistils and stamens. Petal arrangement.—Imbricated. Petal form.—Broad. Petal size.—2.3–2.5 cm length, 1.7–1.9 cm width. Margin type.—Entire. Petal persistence.—5 days without pollination. Appearance.—Satiny with velvety center. Color: Outer petal/floret: Body.—45B. Base.43A (a little orange "velvet"). Reverse side.—43B. Inside petal/floret: Body.—Has spots 46B. Base.—43A to 44B. Reverse side.—43B. Petaloids: Number.—2–5. Color.—44B. Size.—5–19 mm. Flower stem: Petiole. Length.—28 mm. Color.—Red/brown. Strength.—Strong. Character.—The flower cluster is borne well above the foliage, with flowers forming a cluster which is typical of the species, in the form of a rounded grouping on petioles which ascend with flower opening. Petioles radiate for the apex of the peduncle, with the first opened flowers being on top of the cluster. Discoloration after full bloom.—Color becomes a little dull. Effect of heat or rain.—None. Persistence.—Flowers clusters maintain a fresh appearance for approximately 14 days or for about 18 days if matured florets are removed. Petals of mature red flowers dry, shrivel and drop from the plant. Color changes from red to dark red. Fertilization is rare. Disease resistance.—Leaves resistant to botrytis. Fragrance.—None.

*Lasting quality.*—Plant.—More than 16 days. Cut flower.—5 days.

Lasting quality is determined by how long flowering clusters maintain their appearance without picking off old florets. Also observed is the amount of time required from the day the first floret opens to the day when the last floret opens. Time depends on the number of florets found in one cluster and this number with geraniums generally varies from 20 to over 70. The information provided is the amount of time the clusters maintain their appearance without picking off the old florets.

Bud:

*Average diameter.*—10 mm.

*Average depth.*—15 mm.

*Shape.*—Generally urn shaped, similar in shape to other varieties of *Pelargonium zonale.*

*Rate of opening.*—Somewhat quicker than the average of double geraniums.

*Color of petals.*—When petals first divide.—White with dark red veins. When petals begin to unfurl.—Red.

*Sepals.*—Shape.-Long and pointed. Number.—5. (When flowers first open, sepals reflex). Color: Inside.—138A. Outside.—140C.

*Buds and flowering clusters appearing at the same time.*—Young marketable plants.—3 big buds and 2 flowering clusters. Clusters appearing in the greenhouse until the middle of May.—5.5 mature clusters. Clusters appearing outside between May and Spetember.—Average 101 clusters per plant, more when summer is hot.

Reproductive organs:

*Stamens.*—7–9 arranged around the ovaries.

*Anthers:* Size.—2.3 mm. Color.—Red.

*Filaments:* Length.—8 mm. Color.—White.

*Pollen.*—Orange.

*Pistils.*—Number.—1. Stigma.—Articulated with 5–6 splayed segments or lobes. Styles: Length.—9 mm. Color.—Green/red.

*Stigmas.*—Bluish red.

*Fertile.*—Yes.

*Fruit.13* Green, later becoming sand colored. *Length of seed.*—3–4.5 mm.

*Seed color.*—Brown.

What is claimed is:

1. A new and distinct geranium cultivar, substantially as herein described and shown, characterized by its unusually compact and round habit, semi-double dark red flowers with velvety centers and dark green foliage.

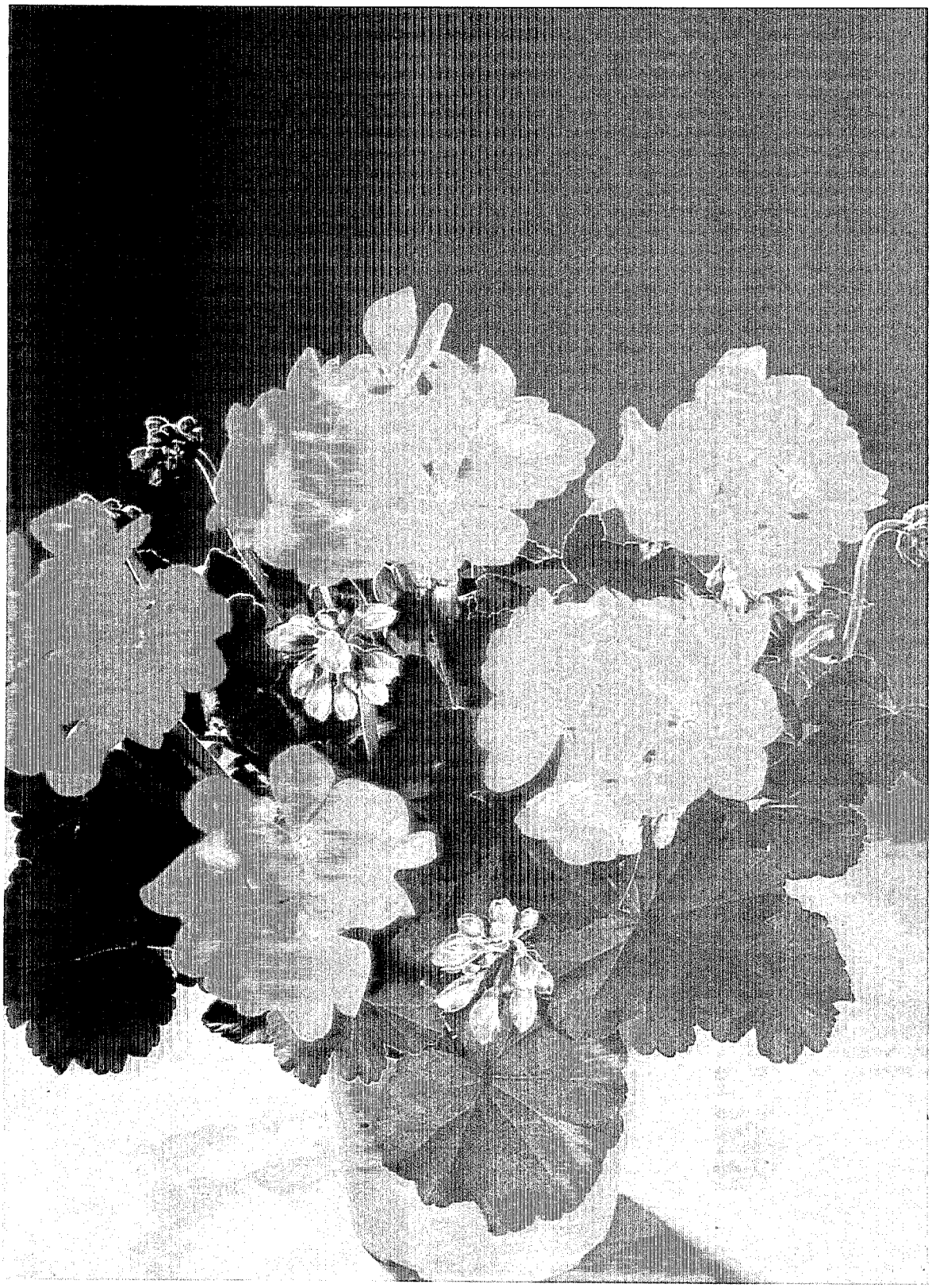

* * * * *